United States Patent [19]

Stähle et al.

[11] 4,239,764
[45] Dec. 16, 1980

[54] SUBSTITUTED 2-PHENYLAMINO-2-IMIDAZOLINES AND SALTS THEREOF

[75] Inventors: Helmut Stähle; Herbert Köppe; Werner Kummer, all of Ingelheim am Rhein; Wolfgang Hoefke, Budenheim, all of Fed. Rep. of Germany

[73] Assignee: Boehringer Ingelheim GmbH, Ingelheim am Rhein, Fed. Rep. of Germany

[21] Appl. No.: 57,582

[22] Filed: Jul. 16, 1979

[30] Foreign Application Priority Data

Jul. 15, 1978 [DE] Fed. Rep. of Germany ....... 2831143

[51] Int. Cl.³ .................. A61K 31/415; C07D 401/02
[52] U.S. Cl. .................................... 424/263; 546/278; 546/329; 546/330; 546/346; 548/351
[58] Field of Search ............... 546/278; 548/351, 348; 424/263

[56] References Cited
U.S. PATENT DOCUMENTS 3,752,810  8/1973  Stahle et al. ................. 548/351 X
3,850,926  11/1974  Stahle et al. ................. 548/351 X

OTHER PUBLICATIONS

Burger, Medicinal Chemistry, 2nd Ed., frontispage and pp. 79–81, Interscience Publishers, Inc. N. Y. 1960.

*Primary Examiner*—John D. Randolph
*Attorney, Agent, or Firm*—Hammond, Littell, Weissenberger & Muserlian

[57] ABSTRACT

Compounds of the formula

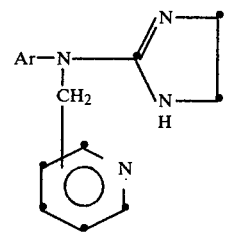

where Ar represents a radical selected from the group consisting of 2,6-dichlorophenyl, 2,5-dichlorophenyl, 2-chloro-6-methylphenyl, 2-chloro-4-methylphenyl, 2,6-dichloro-4-bromophenyl, 4-cyanophenyl, 2,5-dimethoxyphenyl, and 2-methyl-5-fluorophenyl, and non-toxic, pharmacologically acceptable acid addition salts thereof. The compounds as well as their salts are useful as bradycardiacs.

3 Claims, No Drawings

SUBSTITUTED 2-PHENYLAMINO-2-IMIDAZOLINES AND SALTS THEREOF

This invention relates to novel substituted 2-phenylamino-2-imidazolines and non-toxic acid addition salts thereof, to various methods of preparing these compounds, to pharmaceutical compositions containing them as active ingredients, and to methods of using them as bradycardiacs.

More particularly, the present invention relates to a novel class of substituted 2-phenylamino-2-imidazolines represented by the formula

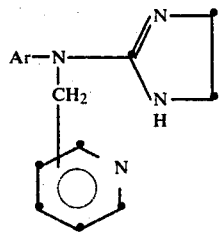

wherein Ar represents a substituent selected from the group consisting of 2,6-dichlorophenyl, 2,5-dichlorophenyl, 2-chloro-6-methylphenyl, 2-chloro-4-methylphenyl, 2,6-dichloro-4-bromophenyl, 4-cyanophenyl, 2,5-dimethoxyphenyl, and 2-methyl-5-fluorophenyl, and non-toxic, pharmacologically acceptable acid addition salts thereof.

The compounds embraced by Formula I may be prepared by the following methods:

Method A

By reacting a 2-phenylimino-imidazolidine of general formula

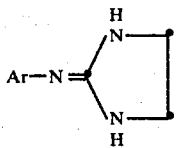

wherein Ar is as defined above in Formula I, with a halide of general formula

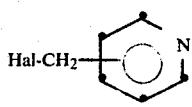

wherein Hal represents a chlorine, bromine, or iodine atom.

Method B

By reacting a compound of general formula

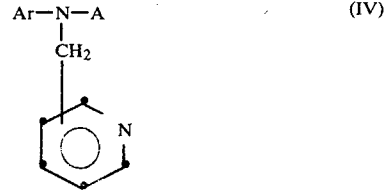

wherein
Ar is as defined above for Formula I and
A is a cyano group or the group

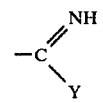

where
Y is an alkoxy group having from 1 to 4 carbon atoms, an alkylthio group having from 1 to 4 carbon atoms, a sulfhydryl group, or an amino group, with ethylenediamine or an acid addition salt thereof.

In the alkylation of the 2-arylimino-imidazolidine of the Formula II pursuant to Method A, the substitution is effected exclusively at the bridge nitrogen atom. In the reaction pursuant to Method B, the structure of the end product is determined by the synthesis. The position of the substituent may also be determined by NMR-spectroscopy. [cf, H. Stähle et al., Liebigs Ann. Chem., 751, 159 et seq. (1971)].

It is advantageous to effect the reaction according to Method A by heating the reaction partners, preferably in the presence of a polar or non-polar organic solvent, to temperatures of about 50° to 150° C. The specific reaction conditions depend to a great extent upon the reactivity of the reaction partners. It is recommended to provide the halide for the alkylation in excess and to perform the reaction in the presence of an acid-binding agent.

Method B is required to be performed at elevated temperatures between 60° and 180° C. Solvents are not necessary. It is advantageous to provide the ethylenediamine or its acid addition salt in excess.

The starting compounds of the Formula II are described in, for example, Belgian Pat. Nos. 623,305, 687,657, and 705,944, incorporated herein by reference.

The starting compounds of the Formula III may be prepared by halogenating the corresponding primary alcohol.

The compounds of the Formula IV are obtained, starting from anilines, by reaction with compounds of Formula III and subsequent reaction of the secondary amines formed thereby with cyanates or thiocyanates, whereby ureas or thioureas are formed. Ureas and thioureas may then be converted by alkylation agents into corresponding isouronium salts or isothiouronium salts. From these acid addition compounds the corresponding isoureas or isothioureas may be obtained with bases. By splitting off water from ureas or splitting off H₂S from thioureas by means of lead or mercury salts, cyanamides are obtained which may be converted into guanidines by addition of ammonia.

The compounds embraced by Formula I are organic bases and therefore form acid addition salts with inorganic or organic acids. Examples of non-toxic, pharmacologically acceptable acid addition salts are those formed with, for example, hydrochloric acid, hydrobromic acid, hydriodic acid, hydrofluoric acid, sulfuric acid, phosphoric acid, nitric acid, acetic acid, propionic acid, butyric acid, caproic acid, valeric acid, oxalic acid, malonic acid, succinic acid, maleic acid, fumaric acid, lactic acid, tartaric acid, citric acid, malic acid, benzoic acid, p-hydroxybenzoic acid, p-aminobenzoic acid, phthalic acid, cinnamic acid, salicylic acid, ascorbinic acid, methanesulfonic acid, 8-chlorotheophylline, or the like.

The compounds of the present invention, that is, the compounds of Formula I above and their non-toxic, pharmacologically acceptable acid addition salts, have useful pharmacodynamic properties. More particularly, they exhibit very strong bradycardiac activity in warm-blooded animals, such as rabbits and rats, including spinal rats as well as intact, narcotized rats, and are therefore useful for the treatment of coronary diseases.

For pharmaceutical purposes the compounds of the present invention are administered to warm-blooded animals perorally or parenterally as active ingredients in customary dosage unit compositions, that is, compositions in dosage unit form consisting essentially of an inert pharmaceutical carrier, galenic incipient, disintegrant, lubricant, or substance for obtaining sustained release, and one effective dosage unit of the active ingredient, such as tablets, coated pills, capsules, wafers, powders, solutions, suspensions, emulsions, syrups, suppositories and the like. One effective dosage unit of the compounds according to the present invention is from 0.0017 to 1.33 mg/kg body weight, preferably 0.017 to 0.5 mg/kg body weight.

The following examples illustrate the present invention and will enable others skilled in the art to understand it more completely. It should be understood, however, that the invention is not limited solely to the particular examples given below.

EXAMPLE 1

2-[N-(2,6-Dichlorophenyl)-N-(α-picolyl)-amino]-2-imidazoline

An amount of 4.6 g (0.02 mol) of 2-(2,6-dichlorophenylimino)-imidazolidine was refluxed together with 4.9 g (150%) of α-picolylchloride hydrochloride in 50 ml of ethyleneglycol monomethyl ether with the addition of 4.3 g of potassium carbonate for 5 hours, under stirring. Then, the solvent was distilled off in vacuo, and the residue was dissolved in 1 N hydrochloric acid. The hydrochloric acid solution was then admixed with ether and while stirring, well alkalized with 50% potassium hydroxide solution. The separated crude substance was then suction filtered. For purification, the residue was dissolved again in 1 N hydrochloric acid, and the hydrochloric acid solution was then fractionally extracted with ether at stepwisely increasing pH values (addition of 2 N sodium hydroxide solution), and from pH 8.5 on, the ether was precipitated in fractions and suction filtered. The ethereal extracts were abandoned. The solid fractions were combined, washed with water, and dried. The yield was 1.5 g (23.4% of theory) of the compound of the formula

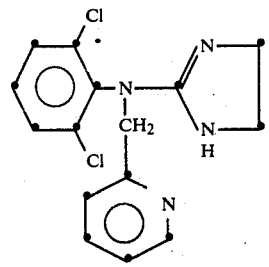

which had a melting point of 171°–172° C.

Thin-layer chromatogram: Rf=0.4.

Mobile system: Benzene:dioxane:ethanol:conc. ammonia=50:40:5:5.

Carrier: Silicagel-G luminous pigment.

Detector: UV and potassium iodoplatinate.

Analysis: $C_{15}H_{14}Cl_2N_4$ (321.22).

|         | C      | H     | Cl     | N      |
|---------|--------|-------|--------|--------|
| Calc.:  | 56.10% | 4.39% | 22.10% | 17.45% |
| Found:  | 56.11% | 4.55% | 21.62% | 17.01% |

In accordance with procedures analogous to that of Example 1, the compounds shown in the table below were also prepared. The melting points refer to the free bases of Formula I.

| Example | Ar | R | M.p.(°C.) | Yield (% of theory) |
|---------|-----|---|-----------|---------------------|
| 2 | 2,6-dichlorophenyl | —CH₂—(pyridin-2-yl) | 182–183 | 34.4 |
| 3 | 2,6-dichlorophenyl | —CH₂—(pyridin-3-yl) | 143–145 | 28.1 |
| 4 | 2,5-dichlorophenyl | —CH₂—(pyridin-2-yl) | 128–129 | 11.7 |

-continued

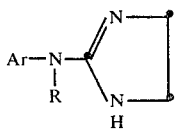

| Example | Ar | R | M.p.(°C.) | Yield (% of theory) |
| --- | --- | --- | --- | --- |
| 5 | 2-chloro-6-methyl-phenyl | —CH₂—(pyridyl) | oil | 20.0 |
| 6 | 2-chloro-4-methyl-phenyl | —CH₂—(pyridyl) | oil | 18.4 |
| 7 | 2,6-dichloro-4-bromo-phenyl | —CH₂—(pyridyl) | 139–141 | 25.0 |
| 8 | 4-cyanophenyl | —CH₂—(pyridyl) | 128–129 | 23.1 |
| 9 | 2,5-dimethoxy-phenyl | —CH₂—(pyridyl) | 129–130 | 33.6 |
| 10 | 2-methyl-5-fluoro | —CH₂—(pyridyl) | 121–123 | 32.4 |

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 11

Coated tablets

The tablet, or pill, core composition can be compounded from the following ingredients:

| Component | Parts |
| --- | --- |
| Compound prepared in Example 1 | 5 |
| Lactose | 65 |
| Corn starch | 130 |
| Secondary calcium phosphate | 40 |
| Soluble starch | 3 |
| Magnesium stearate | 3 |
| Colloidal silicic acid | 4 |
| Total | 250 |

Preparation

The active ingredient is admixed with a portion of the excipients, the mixture is thoroughly kneaded with an aqueous solution of the soluble starch, the moist mass is granulated through a screen, and the granulate is dried. The dry granulate is admixed with the remainder of the excipients, and the composition is compressed in 250 mg tablet cores which are subsequently coated with a thin shell consisting essentially of a mixture of sugar, talcum, and gum arabic. Each coated tablet is an oral dosage unit composition containing 5 mg of the active ingredient.

EXAMPLE 12

Hypodermic solution

The solution can be compounded from the following ingredients:

| Component | Amount |
| --- | --- |
| Compound prepared in Example 1 | 1.0 mg |
| Sodium chloride | 18.0 mg |
| Distilled water   q.s. ad | 2.0 ml |

Preparation

The active ingredient and the sodium chloride are dissolved in the distilled water, the solution is filtered until free from suspended particles, and the filtrate is filled under aseptic conditions and in an atmosphere of nitrogen into 2 cc-ampules which are then sterilized and sealed. The contents of each ampule are an injectable dosage unit composition containing 1 mg of the active ingredient.

EXAMPLE 13

Drop solution

The solution can be compounded from the following ingredients:

| Component | Amount |
| --- | --- |
| Compound prepared in Example 1 | 0.02 g |

| Component | Amount |
| --- | --- |
| Methyl p-hydroxybenzoate | 0.07 g |
| Propyl p-hydroxybenzoate | 0.03 g |
| Demineralized water    q.s. ad | 100.00 ml |

Preparation

The active ingredient and the p-hydroxy-benzoates are dissolved in the demineralized water, the solution is filtered, and the filtrate is filled into 100 ml-bottles equipped with a dropping spout. An amount of 10 cc of the solution is an oral dosage unit composition containing 2 mg of the active ingredient.

Any one of the other compounds embraced by Formula I or a non-toxic, pharmacologically acceptable acid addition salt thereof may be substituted for the particular active ingredient in Examples 11 through 13. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments and that various changes and modifications may be made without departing from the spirit of the invention or the scope of the appended claims.

We claim:

1. A compound of the formula

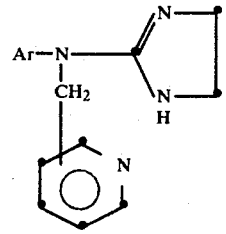

(I)

wherein Ar represents a radical selected from the group consisting of 2,6-dichlorophenyl, 2,5-dichlorophenyl, 2-chloro-6-methylphenyl, 2-chloro-4-methylphenyl, 2,6-dichloro-4-bromophenyl, 4-cyanophenyl, 2,5-dimethoxyphenyl, and 2-methyl-5-fluorophenyl, or a non-toxic, pharmacologically acceptable acid addition salt thereof.

2. A bradycardiac pharmaceutical dosage unit composition consisting essentially of an inert pharmaceutical carrier and an effective bradycardiac amount of a compound of claim 1.

3. The method slowing the heart rate of a warm-blooded animal in need thereof, which comprises perorally or parenterally administering to said animal an effective bracycardiac amount of a compound of claim 1.

* * * * *